(12) United States Patent
Tsukamoto et al.

(10) Patent No.: US 6,471,990 B1
(45) Date of Patent: Oct. 29, 2002

(54) GENE-CONTAINING COMPOSITIONS

(75) Inventors: Makoto Tsukamoto; Takahiro Ochiya, both of Tokyo; Sho Yoshida, Narashino; Takashi Sugimura, Musashino; Masaaki Terada, Tokyo, all of (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/475,086

(22) Filed: Dec. 30, 1999

Related U.S. Application Data (63) Continuation of application No. 08/817,093, filed as application No. PCT/JP95/01734 on Aug. 31, 1995.

(30) Foreign Application Priority Data

Oct. 14, 1994 (JP) .............................................. 6-249469

(51) Int. Cl.$^7$ ........................ A61K 48/00; A61K 9/127; C07H 21/04
(52) U.S. Cl. ........................ 424/450; 514/44; 536/23.1; 536/23.5; 536/23.51
(58) Field of Search .................. 424/450; 514/44; 536/23.1, 23.5, 23.51

(56) References Cited

U.S. PATENT DOCUMENTS 5,928,944 A * 7/1999 Seth et al. .................. 435/375
6,020,202 A * 2/2000 Jessee ........................ 435/458

OTHER PUBLICATIONS

Eric B. Kmiec, Gene Therapy, Investigators have been searching for ways to add corrective genes to cells harboring defective genes. A better strategy might be to correct the defects,240 American Scientist, vol. 87 1999.*

W. French Anderson, Human gene therapy, Nature vol. 392, Supp, Apr. 30, 1998.*

Inder M Verma et al, Gene therapy–promises,problems and prospects,Nature vol. 389,Sep. 18, 1997.*

Charles Coutelle et al,The Challenge of fetal gene therapy, Nature Medicine, vol. 1, No. Sep. 9, 1995.*

* cited by examiner

Primary Examiner—David Guzo
(74) Attorney, Agent, or Firm—Oblon, Spivak, McClelland, Maier & Neustadt, P.C.

(57) ABSTRACT

The present invention provides a gene-containing composition including a gene and a transporter, the transporter being capable of transporting the gene from a pregnant body to fetal cells. When this composition is administered to a pregnant body, birth of offsprings with gene deficiency can be prevented, and gene deficiency can be treated during pregnancy. In animal experiments, when an unknown gene is introduced to animals during their embryogenic stage, the function of the gene in ontogenesis can be elucidated. Moreover, the composition can be used for breeding animals such as pets, industrial animals and cattle.

10 Claims, 11 Drawing Sheets

GENE-CONTAINING COMPOSITIONS

This application is a continuation of Ser. No. 08/817,093 filed May 21, 1997, which is a national stage of PCT/JP95/01734 filed Aug. 31, 1995.

TECHNICAL FIELD

The present invention relates to gene-containing compositions, and more particularly to gene-containing compositions for introducing a gene into fetuses carried by its pregnant mother to express the gene. The invention also relates to a method for introducing a gene into fetuses including those of experimental animals, cattle, and industrial animals.

BACKGROUND ART

In recent years, several methods have been developed for directly introducing foreign genes into animal or human bodies in the hope of applying them to gene therapy for treating diseases caused by genomic abnormalities.

Diseases caused by congenital gene abnormalities such as congenital gene deficiency are preferably treated in the prenatal stage. As regards introduction of genes into prenatal subjects, microinjection into fertilized egg in animal experiments is the sole method that is currently available [Palmitter, R. D. & Brinster, R. L.: Annu. Rev. Genet., 20, 465–499 (1986)].

Although the microinjection method applied to fertilized egg opened the way for introduction of genes into early embryogenic stage, means for introducing foreign genes into fetuses has not yet been developed. Moreover, microinjection method cannot be applied to gene therapy of fetuses in the case of human pregnancy.

Accordingly, an object of the present invention is to develop a method for introducing foreign genes into fetuses in a developmental stage, and another object of the invention is to provide a gene-containing composition for use in such a method.

DISCLOSURE OF THE INVENTION

The present inventors conducted diverse studies of means for administering intended genes to fetuses through its mother's body, and as a result, found that when genes are administered to a mother along with a specific transporter, they can pass through the placental basement membrane serving as a blood barrier between the fetuses and its mother body, and that gene can be introduced into fetal cells to express themselves in situ, leading to completion of the invention.

Accordingly, the present invention provides a gene-containing composition comprising a gene and a transporter, the transporter being capable of transporting the gene from a pregnant body to fetal cells.

The present invention also provides a method for introducing genes to fetal cells by administering the above gene-containing composition to a pregnant body.

BEST MODE FOR CARRYING OUT THE INVENTION

In the present invention, the term "transporter" is used to refer to substances which help the gene to be transported into the target cells. The transporter used in the present invention is capable of introducing genes from the body of a mother to her fetus cells. In more detail, the transporter can introduce genes to fetal cells when it is administered to a pregnant body which carries the fetus. Examples of the transporter include cationic lipopolyamines. Among them, $diC_{10}$–$C_{20}$-alkylamide glycylspermines are preferred. Dioctadecylamide glycylspermines being particularly preferred.

The genes used in the present invention are not particularly limited so long as they can be used for diseases which are preferably treated or prevented during the fetal stage, or they can be used for the gene introduction for the purpose of breeding industrial animals such as experimental animals and cattle as well as pets.

For example, when it has been confirmed that a fetus lacks a certain gene or when it is clear that a fetus lacks a certain gene from its family history, such genes may be used in the present invention. In addition, genes for treating congenital diseases which fetuses suffer from may also be used.

The relationship between congenital genetic diseases and products of deficient genes is shown in the following table.

TABLE 1

| Congenital genetic diseases | Products of deficient genes |
|---|---|
| Familial hypercholesterolemia | Low density lipoprotein receptor |
| Metabolic error in lipids | Apolipoprotein |
| Phenylketonuria | Phenylalaninhydroxylase |
| Hemophilia A | Factor VIII |
| Hemophilia B | Coagulation Factor IX |
| Ornithinetranscarbamoylase deficiency | Ornithinetranscarbamoylase |
| Gene tyrosinemia | Fumarylacetoacetate hydroxylase |
| Cystic pulmonary fibrosis | Transmembrane Conductance regulatory factor through cystic pulmonary fibrosis |
| Duchenne type muscular dystrophy | Minidystrophine gene products |
| Li-Fraumeni syndrome | p53 protein |
| Retinoblastoma | RB protein |
| Lesch-Nyhan syndrome | Hypoxanthin guanine phosphoribosyl transferase |
| Adenosine deaminase deficiency | Adenosine deaminase |
| Nieman-Pick disease | Sphingomyelin phosphodiesterase I |
| Tay-Sacks disease | Hexosaminidase A |
| $\alpha_1$Antitrypsin deficiency | $\alpha_1$-Antitrypsin |
| Antithrombin III deficiency | Antithrombin III |
| Carbamyl phosphate synthesizing enzyme deficiency | Carbamyl phosphate synthesizing enzyme |
| Growth hormone deficiency (Type IA) | Growth hormone |
| Thyroglobulin deficiency | Thyroglobulin |
| 21-hydroxylase deficiency (Congenital adrenal hyperplasia) | 21-Hydroxylase |
| Pyruvate dehydrogenase deficiency | Pyruvate dehydrogenase |

Moreover, the composition and method of the present invention can be used in gene introduction models by applying them to animals with spontaneous genetic diseases or knockout animals (animals which are artificially forced to have gene dysfunctions). In addition, in the treatment of viral hepatitis or infant malignant tumors, antisense oligonucleotides which suppress viral gene products in the presence of viral hepatitis (A, B, or C) and other antisense oligonucleotides which suppress expression of oncogenes which generate infant malignant tumors such as Wilm's tumors and neuroblastoma and genes which cause other diseases.

As for examples of genes which are introduced into animal bodies, there are (1) genes for producing pharmaceuticals in animal bodies, (2) genes for improving quality of the meat, physical constitution, fur, milk of animals, (3) gene materials for studying the function of a gene by deleting or introducing the gene into a viviparous animal, and (4) gene materials for restoring expression of gene in an animal with gene deficiency which causes fetal death in the uterus.

The fetuses include those of mammals except humans such as dogs, bovines, horses, goat, sheep, monkeys, cats, pigs, mice, and rats, as well as those of humans.

The form of genes to be used is not particularly limited. However, plasmids which are constituted so as to express the genes are particularly preferred in view of ease in introduction and expression. A combination of a strong promoter and/or enhancer and a gene is more preferable because expression is promoted. If promoters which are highly organ specific are used, a so called organ targeting may also be possible in which genes are expressed in a specific organ.

In the gene-containing composition of the present invention, a gene and a transporter may be present in the form of a mixture. Alternatively, they may be present in the form that a transporter which is in a miselle state and a gene are mixed. Moreover, a transporter which has formed a liposome and a gene may be mixed. If a transporter has formed a liposome, it is preferable that genes are present in the inner liposome, in the membrane thereof, or in the surface of the membrane. Examples of methods for forming liposomes include vortexing, sonication, reverse-phase evaporation, freeze-drying, humidification, methods of using polyols, mechanochemical methods, lipids dissolving methods and spray-drying. When liposomes are prepared, phospholipid such as dimyristoylphosphatidylglycerols, phosphatidylcholines, phosphatidylethanolamines, phosphatidyl inositols, phosphatidic acid, etc., cholesterols, $\alpha$-tocopherols, dicetyl phosphates and stearylamines may be added as membrane-constituting components.

The proportion of a gene and a transporter varies depending on their identity. In general, it is preferred that a transporter be incorporated in an amount of 1–100 nmol and particularly 5–10 nmol per $\mu$g of DNA.

The composition of the present invention is preferably administered to a pregnant body by injection, and particularly preferably, by arterial injection or intravenous injection. Moreover, the composition may be administered via a catheter into the blood vessel of the mother. The time for administration is not particularly limited if it is during pregnancy. It is, however, particularly preferred that the composition be administered during the organogenic period.

The composition of the present invention, after administered to a mother's body, passes through the basement membrane of the placenta, then to the umbilical cord, and finally to the fetus, thereby introducing genes to fetal cells. It has been confirmed that the genes thus introduced are present and expressed in cells of the newborn after transfer.

Accordingly, the composition of the present invention is useful in experiments of introducing genes into fetuses, in prevention of the birth of gene-deficient babies, and in prevention and treatment of gene deficiency of fetuses. Also, the composition is useful in breeding industrial animals and pets.

EXAMPLES

The present invention will next be described in more detail by way of examples, which should not be construed as limiting the invention.

Example 1

(1) Plasmid for use in Introduction

An SV40-chloramphenicol acetyltransferase (CAT) plasmid [4752bp, product of Promega] was used.

(2) Transporter

Dioctadecylamido glycylspermine (DOGS) [Proc. Natl. Acad. Sci. USA 86 (1989) p6983] (Transfectum, product of Biosepra Inc.) was used.

(3) Preparation of the Composition of the Present Invention

To 133 $\mu$g of an SV40-CAT plasmid, 250 $\mu$l of an aqueous 0.3 M NaCl solution was added to prepare a plasmid solution. Separately, 20 $\mu$l of 96% ethanol was added to 500 $\mu$g of DOGS and incubated at room temperature for 5 minutes. To the resulting solution, 180 $\mu$l of purified water was added to prepare a DOGS solution. To a solution containing 200 μl of the DOGS solution and 250 μl of purified water, the plasmid solution was added. The mixture was mechanically shaken in a vortex mixer to obtain the composition of the present invention.

(4) Introduction of a Gene i) The composition prepared as described above was injected into the tail vein of each pregnant female mouse (body weight: about 30 g, Charles River Co.) at day 9.5 postcoitus (P.C.). Seven days after (at day 16.5 P.C.), the maternal liver was taken out. Also, the fetus was isolated by cesarean section. Genomic DNA was extracted from the liver and the fetus, and subjected to Southern blot analysis for the presence of the CAT genes. Genomic DNA was collected in accordance with the procedure described in Proc. Natl. Acd. Sci. USA 83, 4993–4997 (1986). The DNA which had been completely digested by restriction enzyme SalI and that which had not been digested were separated by electrophoresis on 1% agarose gel, and then transferred onto Hybond-N+nylon membrane (product of Amersham). Blots were hybridized using a SV40-CAT fragment labelled with $^{32}P$ (1908 bP, Hind III fragment) as a probe. Specific bands were detected on an autoradiogram.

Figure 1:
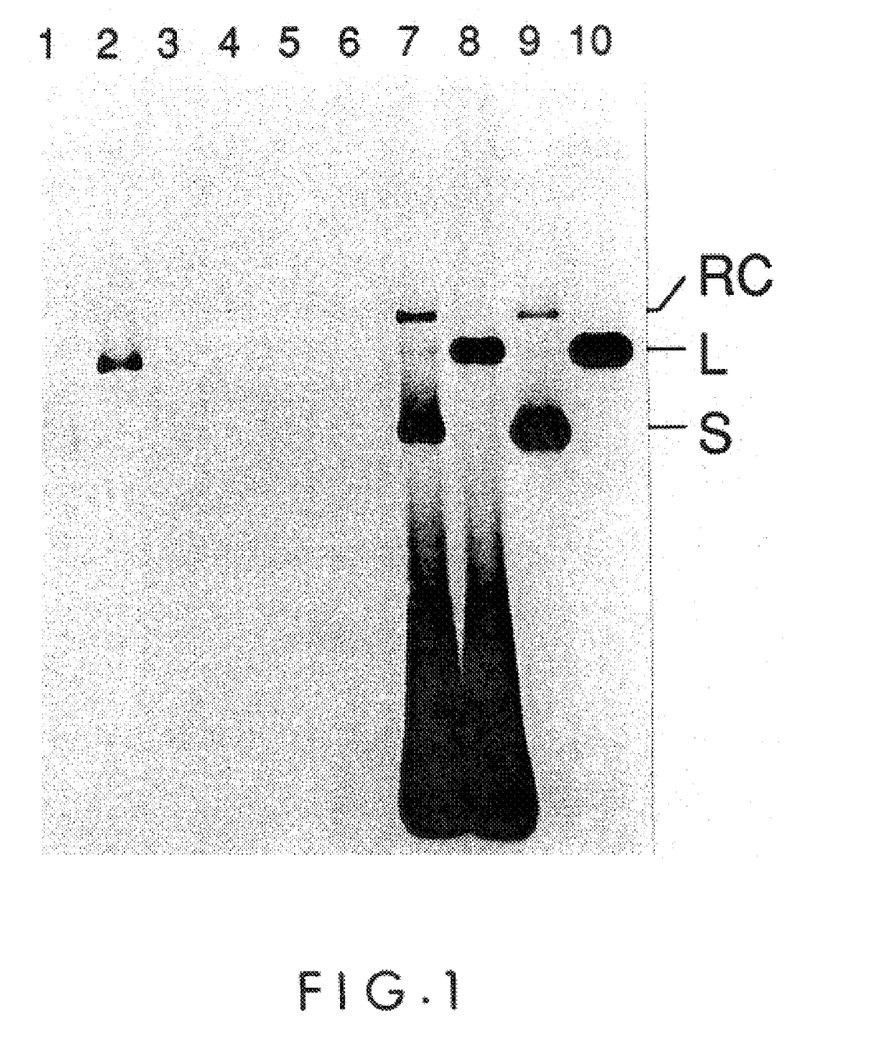
FIG. 1 shows the results of Southern blot analysis of genomic DNA of a fetus and the maternal liver after administration of the composition of the present invention.

As a result, it was confirmed that an foreign gene, SV40-CAT plasmid, was introduced into fetal cells as shown in FIG. 1.

Figure 2:
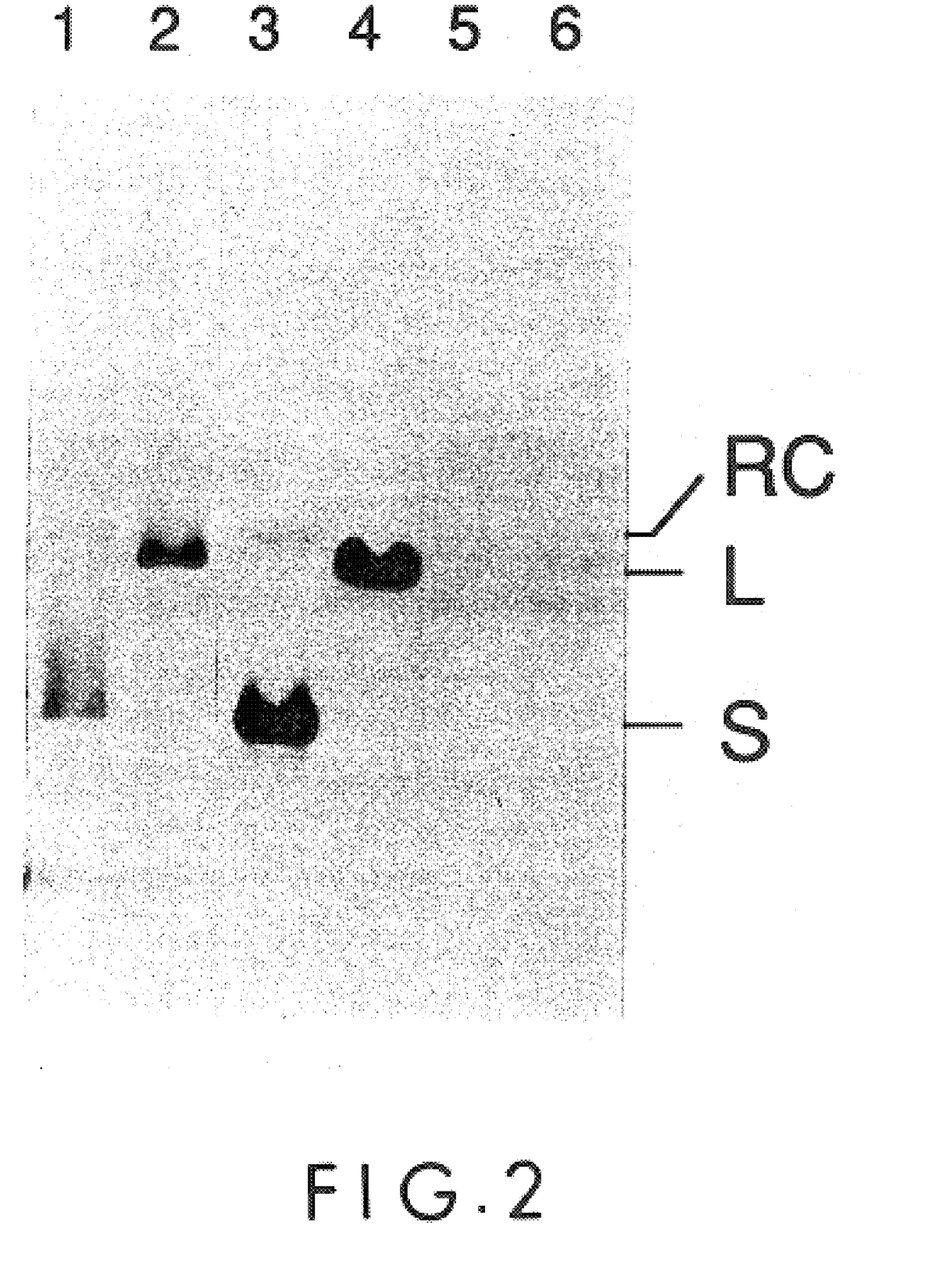
FIG. 2 shows the results of Southern blot analysis of genomic DNA of a fetus and the maternal liver after administration of a foreign gene alone.
Figure 3:
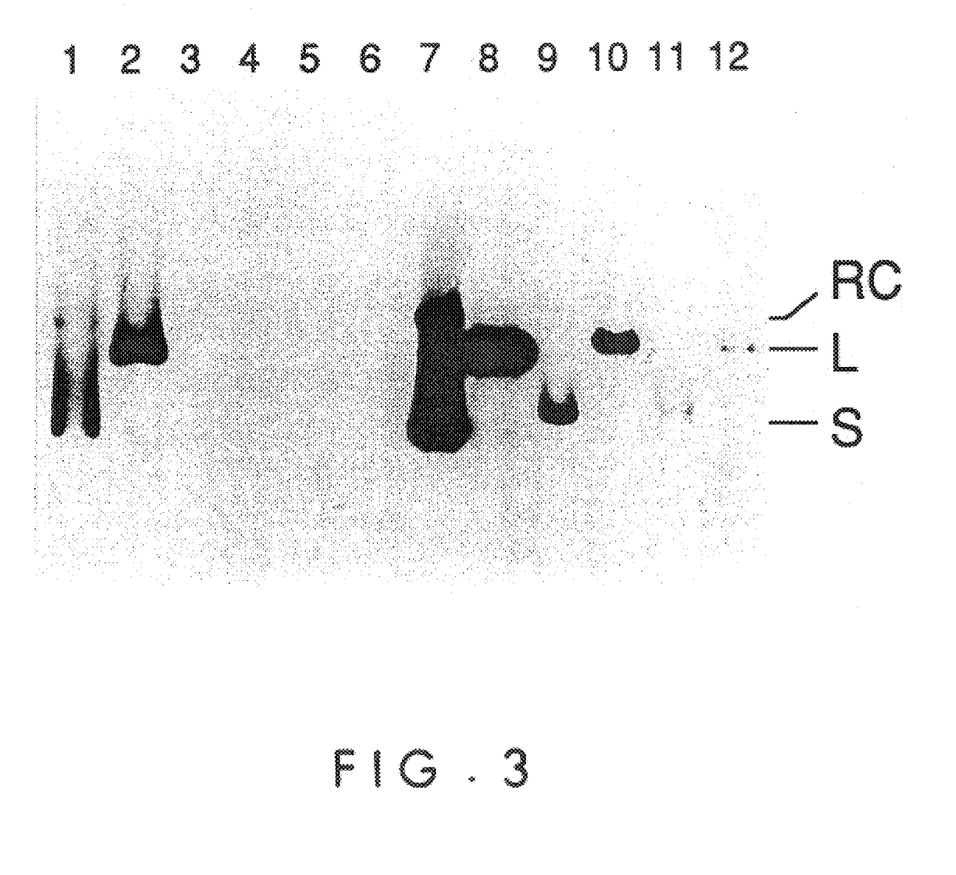
FIG. 3 shows the results of Southern blot analysis of genomic DNA of a fetus when the composition is administered at days 3, 6, 9, 12, and 15 postcoitus.

In FIG. 1, lanes 1 and 2 are of genomic DNA from control SV40-CAT plasmids (33 pg), lanes 3 and 4 are from untreated maternal livers, lanes 5 and 6 are from untreated fetuses, lanes 7 and 8 are from the maternal livers administered with the composition of the present invention, and lanes 9 and 10 are from treated fetuses.

ii) Results are shown in FIG. 2, which were obtained in an experiment in which a neat SV40-CAT plasmid was administered to pregnant mice in a manner similar to that described in i) above without being blended with a transporter. From FIG. 2, it is apparent that SV40-CAT plasmids cannot be effectively introduced into fetal cells in the absence of a transporter. In FIG. 2, lanes 1 and 2 are of genomic DNA from control SV40-CAT plasmids (33 pg), lanes 3 and 4 are from the maternal livers to which only plasmids were administered, and lanes 5 and 6 are from their fetuses.

iii) FIG. 3 shows the results obtained in an experiment similar to that of i) above in which the composition was administered at different times. From FIG. 3, it is apparent that almost no genes were introduced when the composition was administered during the period from day 3 to day 6 P.C., that genes became to be introduced after about day 9 P.C., and that the efficiency in introducing the genes was the highest on around day 9 P.C. In FIG. 3, lanes 1 and 2 are of genomic DNA from control SV40-CAT plasmids (33 pg), lanes 3 and 4 are from fetuses to which the gene was introduced at day 3 ,P.C., lanes 5 and 6 are from those at day 6 P.C., lanes 7 and 8 are from those at day 9 P.C., lanes 9 and 10 are from those at day 12 P.C., and lanes 11 and 12 are from those at day 15 P.C.

Example 2

In a manner similar to that described in Example 1, the composition of the present invention obtained in Example 1 (3) was administered to mice at day 9 P.C. Genomic DNA was extracted from fetuses at day 16.5 P.C., newborn mice, and one month-old mice. Southern blot analysis was performed.

Figure 4:
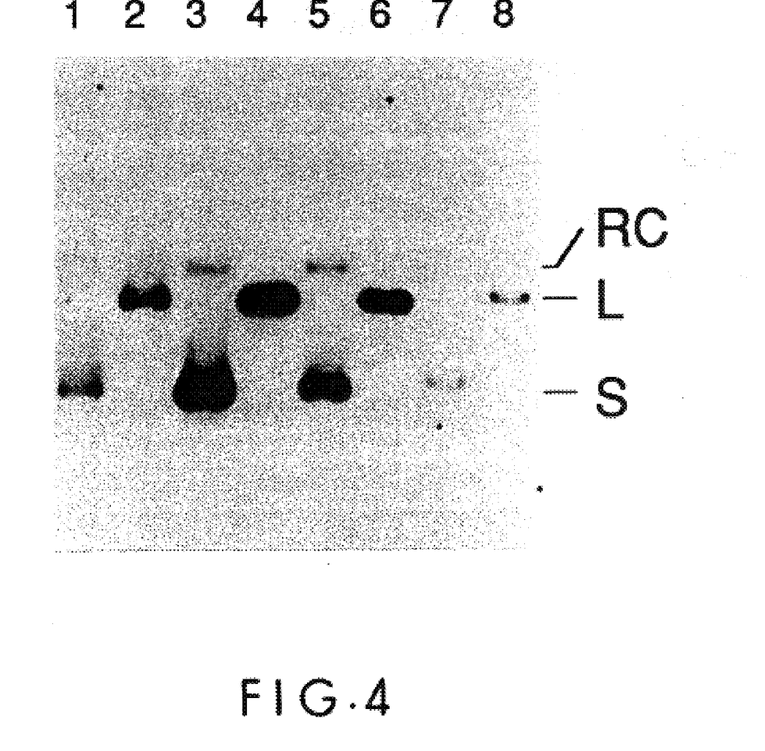
FIG. 4 shows the results of Southern blot analysis of genomic DNA extracted from a mouse fetus, a newborn mouse, and a one month-old young mouse when the composition of the present invention was administered to their mothers' bodies at day 9 postcoitus.
Figure 5:
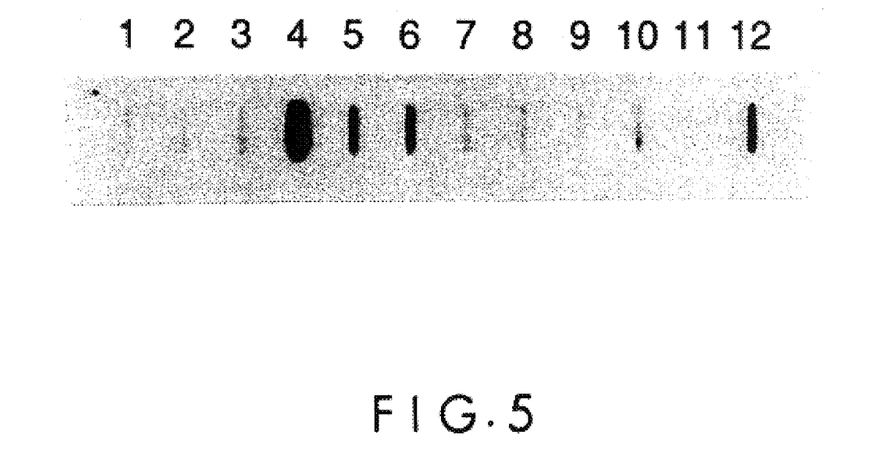
FIG. 5 shows the results of Slot blot analysis of genomic DNA extracted from organs of the one month-old young mouse shown in FIG. 4.

As a result, it was confirmed that genes introduced were present in all cases as shown in FIG. 4. In FIG. 4, lanes 1 and 2 are of genomic DNA from control SV40-CAT plasmids (33 pg), lanes 3 and 4 are from fetuses at day 16.5 P.C., lanes 5 and 6 are from newborn mice, lanes 7 and 8 are from one month-old mice. Next, genomic DNA was extracted from a variety of organs of the one-monthold mice and subjected to Slot blot analysis. It was found that the genes had been introduced to various organs. In FIG. 5, lane 1 is of genomic DNA from the brain, lane 2 is from the thyroid gland, lane 3 is from the thymus gland, lane 4 is from the heart, lane 5 is from the lung, lane 6 is from the liver, lane 7 is from the spleen, lane 8 is from the pancreas, lane 9 is from the kidney, lane 10 is from the small intestine, line 11 is from the uterus, and lane 12 is from the muscle.

Example 3

Expression of gene SV40-CAT introduced as described in Example 1-i) was confirmed by Northern blot analysis.

Figure 6:
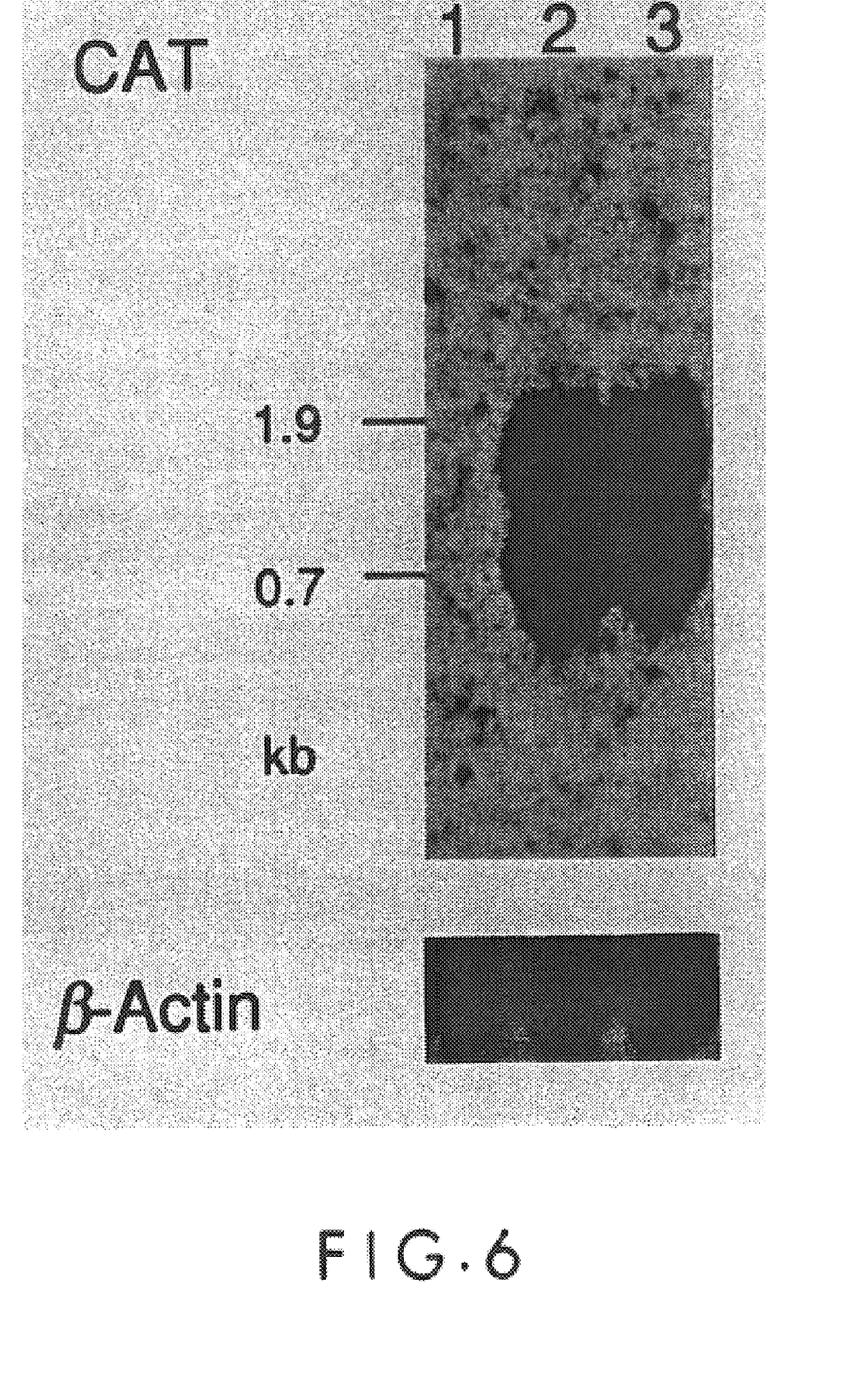
FIG. 6 shows the results of Northern blot analysis of RNA extracted from a mouse fetus and a newborn mouse when the composition of the present invention was administered to their mothers' bodies at day 9 postcoitus.

Briefly, RNA was extracted from the whole bodies of fetuses or newborn mice to which the gene was introduced in a manner similar to that described in Example 1-i) using isogen (product of Nippongene). The RNA (20 pg) was separated by electrophoresis on 1% agarose gel, and then transferred onto a nitrocellulose membrane (Nitroplus Cellulose membrane, product of Micron Separations Inc.). In a manner similar to that described in Example 1, hybridization was performed using an SV40-CAT fragment labelled with $^{32}p$ as a probe. As a result, transcription from the introduce gene to RNA was found in all fetuses and neonatal mice. In FIG. 6, lane 1 represents untreated fetuses, lane 2 represents fetuses to which the gene had been introduced, and lane 3 represents newborn mice to which the gene had been introduced.

Next, protein samples were extracted from the whole bodies of fetuses and newborn mice to which the gene was introduced as described in Example 1-i), and they were assayed for the expression of an foreign gene, i.e., the enzymatic activity of CAT. Briefly, the amount of protein in each sample was made equal to each other, and the samples were subjected to a heat treatment at 60° C. for 5 minutes so as to deactivate the intrinsic inhibitory factor of CAT. The activity of CAT was assayed by known means (Zhu, N., Liggitt, D., Liu, Y. & Debs, R., Science 261, 209–211 (1993); and Gorman, C. M., Moffat, L.F. & Howard, B.H., Mol. Cell. Biol. 2, 1044–1051 (1982)). Enzymatic activity was measured by adding 200 nmol of acetyl coenzyme A to a final amount of 150 μl of chloramphenicol labelled with 0.1 μCi of $^{14}C$ (55 mCi/mmol).

Figure 7:
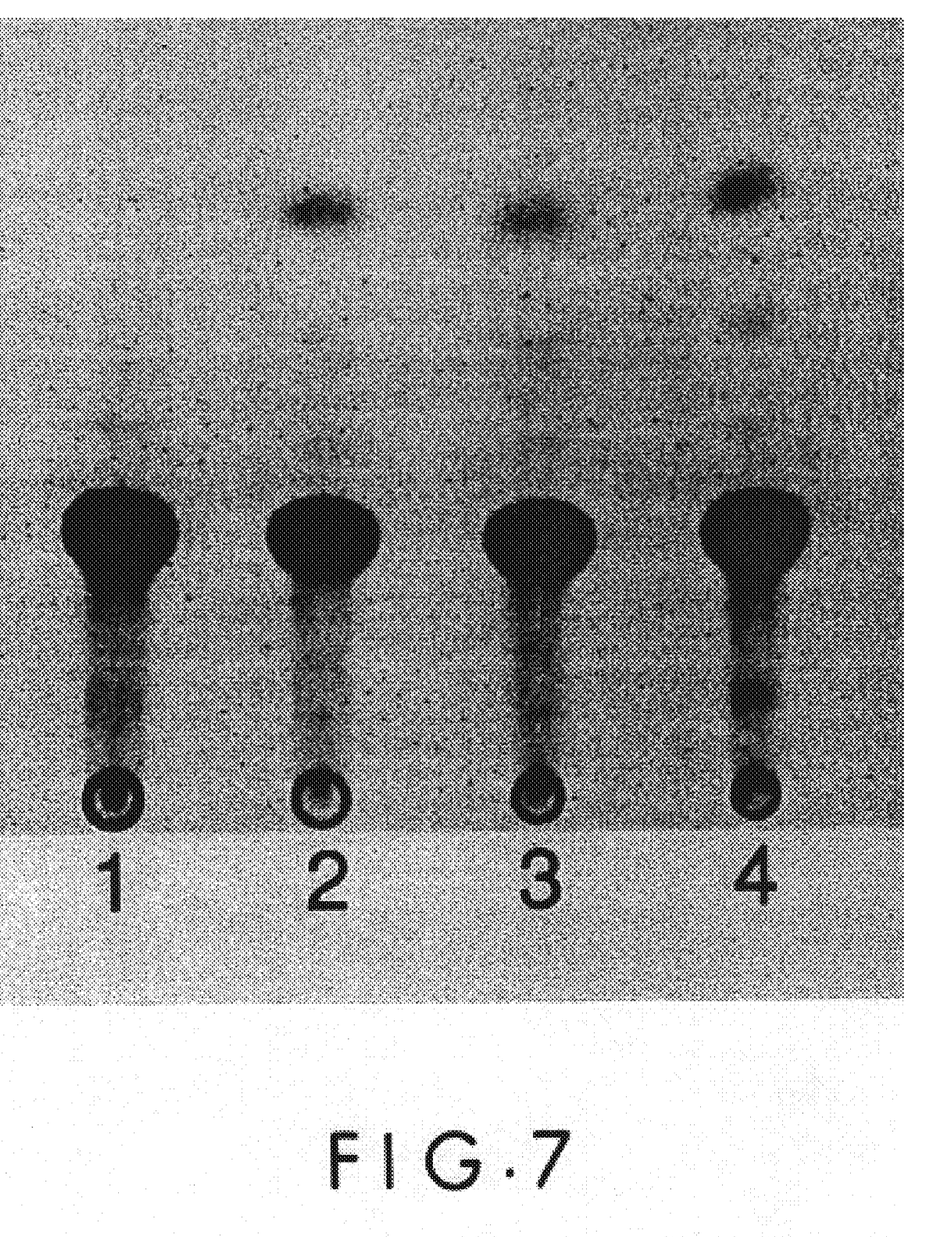
FIG. 7 shows CAT activity of the proteins extracted from a mouse and a newborn mouse to which SV40-CAT gene has been introduced.
Figure 8A:
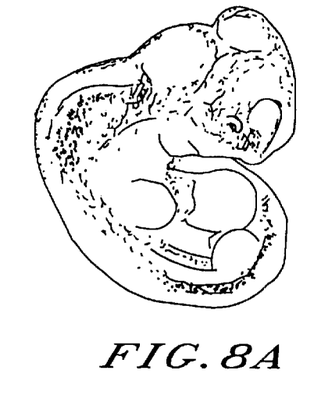
FIG. 8 (parts A–F) shows histchemical profiles obtained by staining, with X-gal, expression of β-actin-lacZ which has been introduced into fetuses by administering the composition of the present invention to their mothers at day 8.5 postcoitus.
Figure 8B:
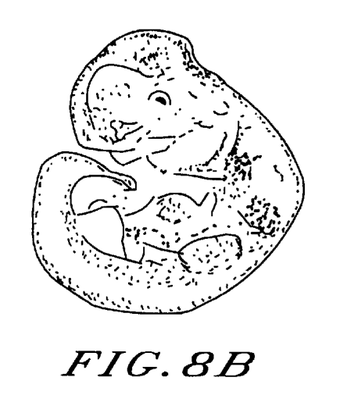
Figure 8C:
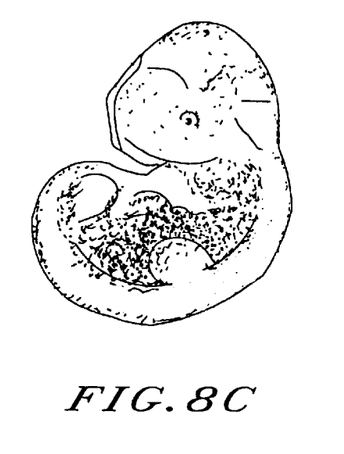
Figure 8D:
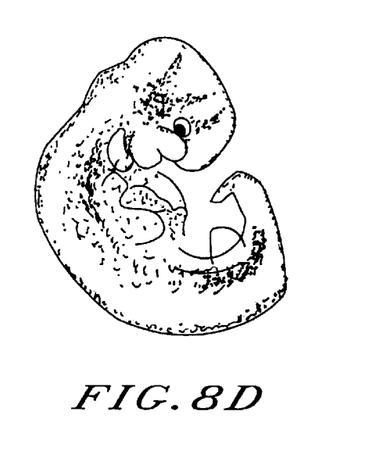
Figure 8E:
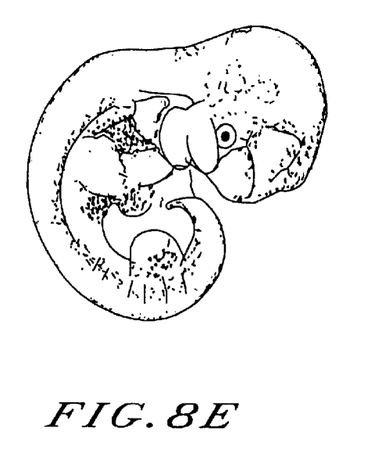
Figure 8F:
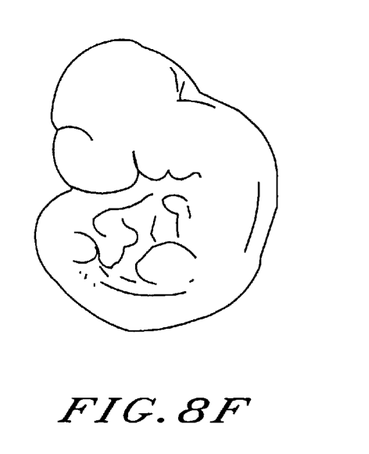
Figure 9G:
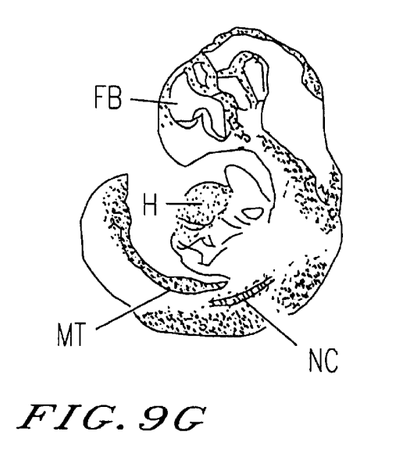
FIG. 9 (parts G–K) shows tissue slices of mouse fetuses in which β-actin-lacZ which has been introduced is expressed.
Figure 9H:
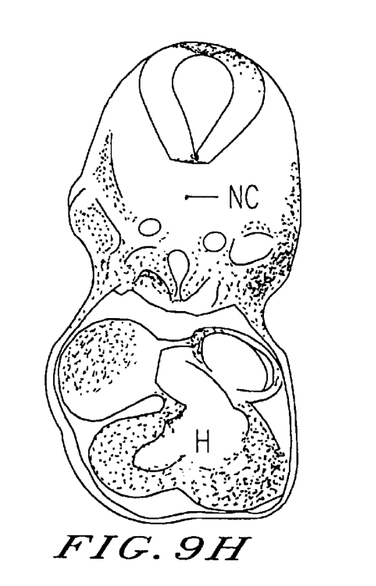
Figure 9I:
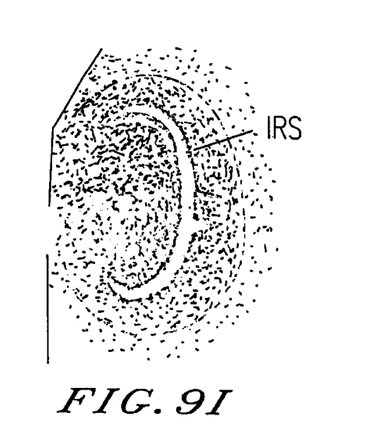
Figure 9J:
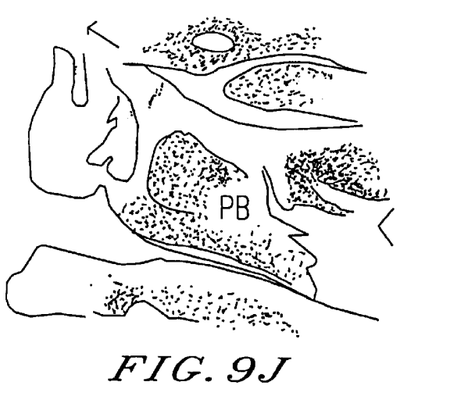
Figure 9K:
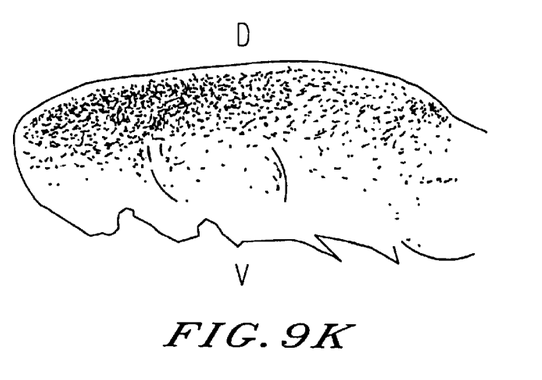

As a result, expression of the introduced gene was confirmed in all fetuses and newborn mice, which demonstrates that the CAT protein had been produced. In FIG. 7, lane 1 represents untreated fetuses, lane 2 represents fetuses to which the foreign gene had been introduced, lane 3 represents newborn mice to which the foreign gene had been introduced, and lane 4 represents control CAT of 0.2 μU of CAT as control.

Example 4

As a plasmid to be introduced, an lacZ plasmid containing a chicken M-actin promoter (Sakura, H. et al., Proc. Natl. Acad. Sci. U.S.A. 86, 5758–5762 (1989) was used. A composition according to the present invention was prepared in a manner similar to that described in Example 1(3) using 133 jug of an lacZ plasmid and 400 nmol of DOGS.

The composition thus obtained was injected into the tail vein of each pregnant female mouse at day 8.5 P.C. to introduce the gene. The fetus was isolated at day 10.5 P.C.

A Cheng's method was employed to detect β-actin-lacZ activity by staining with X-gal (Cheng, T. C., Wallace, M. C., Merlie, J. P. & Olsow, E. N., Science 261, 215–218 (1993)). Frozen slices were prepared after the stained fetus was soaked in 4° C. phosphate-buffered saline containing 20% sucrose and 0.2% dextrose. Continuous slices were cut to a thickness of 30 μm, and suitable slices were selected for counter staining with nuclear fast red. The stained profiles were observed.

Results of the whole body staining of gene-introduced mice are shown in FIG. 8, and results of slice staining are shown in FIG. 9. As shown in these figures, β-actin-lacZ activity was expressed widely in various organs of the fetuses. In FIG. 8, a to e show fetuses to which the gene had been introduced, and f shows an untreated control fetus. In FIG. 9, g shows a slice of the whole body of a fetus cut in the longitudinal direction, h shows a forehead-cut slice of the whole body of a fetus cut through the heart, i shows a slice of the right optic vesicle (enlarged), j shows a slice of the pancreatic bud (enlarged), k shows a slice of the left forelimb bud (enlarged), FB indicates the forebrain, H indicates the heart, MT indicates the mesonephric tubules, Nc indicates the notochord, IRS indicates intra-retinal space, PB indicates the pancreatic bud, D indicates the dosal aspect, and V indicates the ventral aspect.

Example 5

As a gene to be introduced, an HST-1 gene was used. Upon use, the recombinant expression vector which contains HST-1 cDNA and SR-α promoter was constructed, and administered to a pregnant body. The offspring mice were studied as to whether the HST-1 gene was expressed. Since HST-1 gene product is known to increase the number of platelets, the presence or absence of expression was determined by counting the number of platelets.

(1) Gene to be Introduced

An expression plasmid containing an HST-1 gene ligated with an SR-a promoter was used.

(2) Preparation of the Composition of the Present Invention

The procedure of Example 1(3) was repeated except that 133 pg of the SR-Δ-HST-1 gene was used.

(3) Introduction of the Gene

Figure 10:
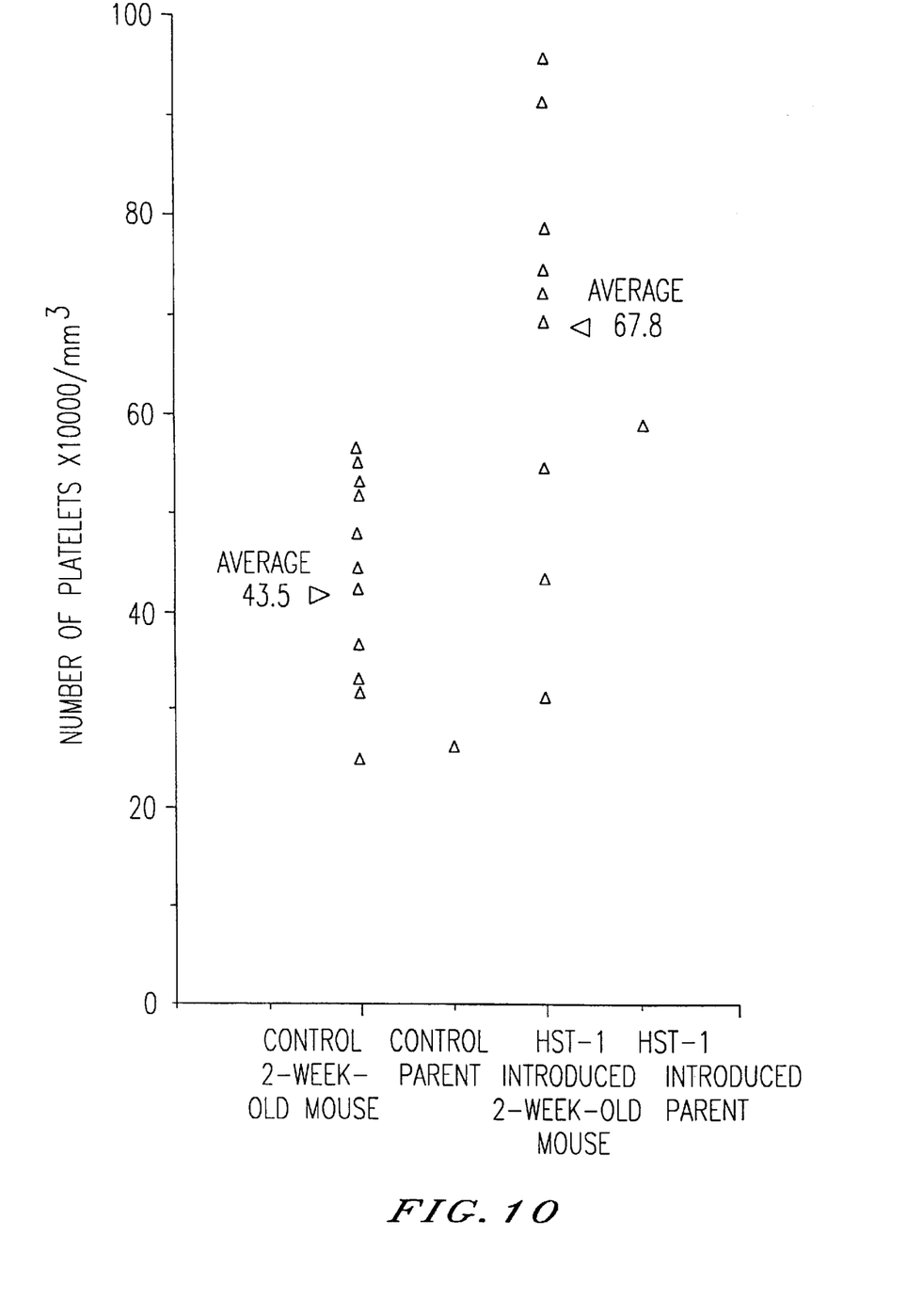
FIG. 10 is a graph showing numbers of platelets of a two week-old mouse and its mother mouse to which SR-Δ-HST-1 gene has been introduced (wherein blood was collected from the heart).
Figure 11:
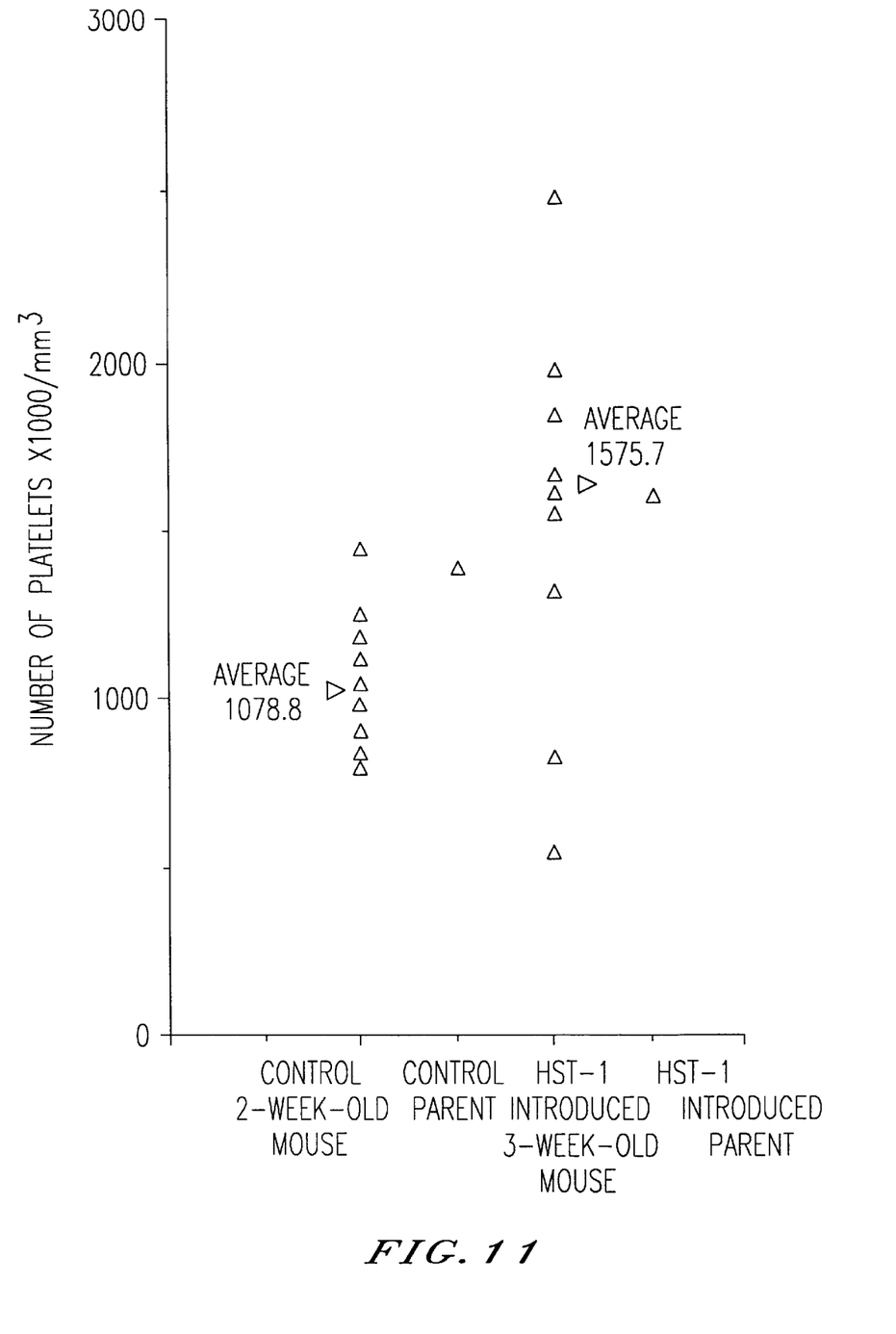
FIG. 11 is a graph showing numbers of platelets of a three week-old mouse and its mother mouse to which SR-Δ-HST-1 gene has been introduced (wherein blood was collected from the orbital vein).

The composition prepared as above was injected into the tail vein of each pregnant female mouse at day 10.5 P.C. to introduce the gene. The number of platelets of the offspring mice was measured on week 2 and week 3 after their birth. At the same time, the number of their mothers' platelets was also measured. The results are shown in FIGS. 10 and 11. FIG. 10 shows the results on the blood collected from the heart, and FIG. 11 shows those of the blood collected from the orbital vein.

From these results, it is clear that the number of platelets of the young mice to which the HST-1 gene was introduced was higher than that of control mice. This demonstrates that the HST-1 gene was introduced into the young mice and that the gene was expressed in the mice.

Figure 12:
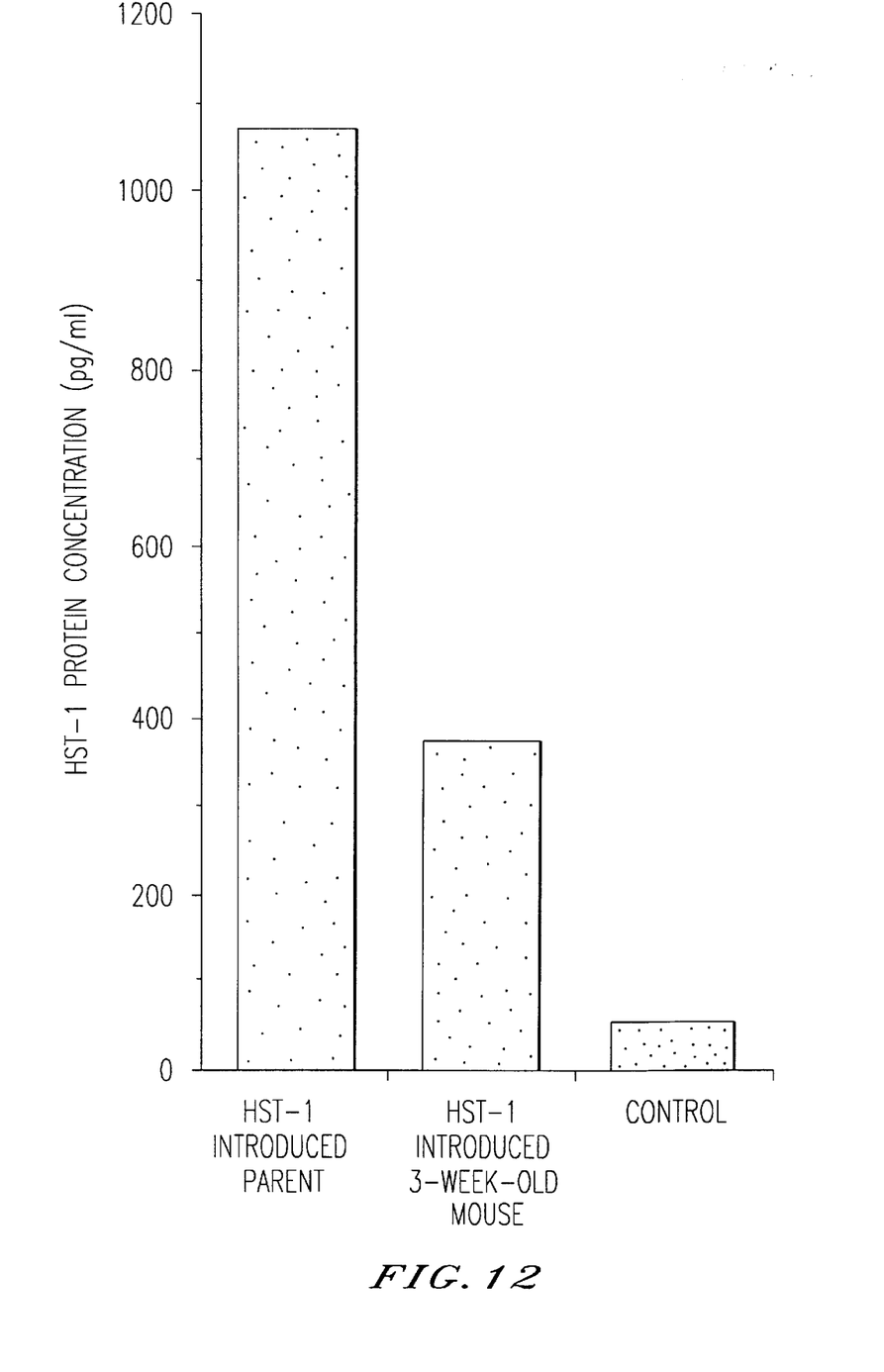
FIG. 12 is a graph showing the HST-1 protein concentration in the sera of three week-old mice and their mother mouse to which SR-Δ-HST-1 gene has been introduced.

The HST-1 protein in sera of 3-week-old-mice was measured by ELISA. Briefly, using 50 μl of serum collected from each 3-week-old mouse and known methods, ELISA was performed to measure the amount of the HST-1 protein (Proc. Natl. Acad. Sci. USA, vol. 91, pp112368–12372, December 1994). The results are shown in FIG. 12. The data in FIG. 12 shows that the HST-1 protein was detected in the blood of the young mice born to their mothers to which the HST-1 gene was introduced.

Industrial Applicability

When the composition of the present invention is administered to a pregnant body, birth of offsprings with gene deficiency can be prevented, and in addition, gene deficiency can be treated during pregnancy. In animal experiments, when an unknown gene is introduced to animals during their embryogenic stage, the function of the gene in ontogenesis can be studied. Moreover, the composition can be used for producing physiologically active substances such as pharmaceuticals in animal bodies or increasing the production of such substances. Thus, it is possible to breed animals by improving their physical constitution, quality of meat, milk, and furs.

What is claimed is:

1. A gene-containing composition, which comprises:
   a) an operable gene; and
   b) a di-$C_{10}$–$C_{20}$-alkylamide glycylspermine;
      the di-$C_{10}$–$C_{20}$-alkylamide glycylspermine being present in an amount of about 1 to 100 nmol per μg of DNA.

2. The gene-containing composition of claim 1, wherein said di-$C_{10}$–$C_{20}$-alkylamide glycylspermine is dioctadecylamide glycylspermine.

3. The gen-containing composition of claim 1, wherein said di-$C_{10}$–$C_{20}$-alkylamide glycylspermine is present in an amount of about 5 to 10 nmol per μg of DNA.

4. A gene-containing composition, which comprises:
   a) an operable gene; and
   b) a di-$C_{10}$–$C_{20}$-alkylamide glycylspermine;
      wherein the operable gene is contained in a plasmid and the plasmid further contains a promoter and an enhancer, said promoter being organ-targeting.

5. A gene-containing composition, which comprises:
   a) an operable gene; and
   b) a di-$C_{10}$–$C_{20}$-alkylamide glycylspermine;
      the di-$C_{10}$–$C_{20}$-alkylamide glycylspermine and said operable gene being incorporated in micelles.

6. The gene-containing composition of claim 5, wherein said di-$C_{10}$–$C_{20}$-alkylamide glycylspermine is dioctadecylamide glycylspermine.

7. The gene-containing composition of claim 5, wherein said di-$C_{10}$–$C_{20}$-alkylamide glycylspermine is present in amount of about 1 to 100 nmol per μg of DNA.

8. A gene-containing composition, which is obtained by mixing a solution containing an operable gene, and a di-$C_{10}$–$C_{20}$-alkylamide glycylspermine-containing solution and shaking the same, said di-$C_{10}$–$C_{20}$-alkylamide glycylspermine being present in an amount of from 1 to 100 nmol per μg of DNA.

9. A gene-containing composition, which is obtained by mixing a solution containing an operable gene, and a di-$C_{10}$–$C_{20}$-alkylamide glycylspermine-containing solution and shaking the same;
   wherein the operable gene is contained in a plasmid and the plasmid further contains a promoter and an enhancer, said promoter being organ-targeting.

10. A gene-containing composition, which is obtained by mixing a solution containing an operable gene, and a di-$C_{10}$–$C_{20}$-alkylamide glycylspermine-containing solution and shaking the same, said di-$C_{10}$–$C_{20}$-alkylamide glycylspermine and said operable gene being incorporated in micelles.

* * * * *